US010034746B2

(12) United States Patent
Figulla et al.

(10) Patent No.: US 10,034,746 B2
(45) Date of Patent: Jul. 31, 2018

(54) VALVE PROSTHESIS FOR THE REPLACEMENT OF AN ATRIOVENTICULAR VALVE

(71) Applicants: Hans Rainer Figulla, Jena (DE); Alexander Lauten, Jena (DE)

(72) Inventors: Hans Rainer Figulla, Jena (DE); Alexander Lauten, Jena (DE)

(*) Notice: Subject to any disclaimer, the term of this patent is extended or adjusted under 35 U.S.C. 154(b) by 48 days.

(21) Appl. No.: 14/653,050

(22) PCT Filed: Dec. 16, 2013

(86) PCT No.: PCT/EP2013/076766
§ 371 (c)(1),
(2) Date: Jun. 17, 2015

(87) PCT Pub. No.: WO2014/095761
PCT Pub. Date: Jun. 26, 2014

(65) Prior Publication Data
US 2015/0335421 A1 Nov. 26, 2015

(30) Foreign Application Priority Data
Dec. 17, 2012 (EP) .................................... 12008390

(51) Int. Cl.
A61F 2/24 (2006.01)

(52) U.S. Cl.
CPC .......... *A61F 2/2409* (2013.01); *A61F 2/2418* (2013.01); *A61F 2/2412* (2013.01); *A61F 2230/0006* (2013.01); *A61F 2230/0008* (2013.01); *A61F 2230/0065* (2013.01); *F04C 2270/0421* (2013.01)

(58) Field of Classification Search
CPC .................. A61F 2/2409; A61F 2/2418; A61F 2230/008; A61F 2/2412; A61F 2/2445; A61F 2210/0014; A61F 2220/0016; A61F 2230/005; A61F 2/243; A61F 2230/0093;
(Continued)

(56) References Cited

U.S. PATENT DOCUMENTS 5,411,552 A    5/1995  Andersen et al.
2007/0142907 A1*  6/2007  Moaddeb .............. A61F 2/2445
                                                       623/2.11
(Continued)

FOREIGN PATENT DOCUMENTS

EP    1 225 510 A2    7/2002
EP    1 980 220 A1   10/2008
(Continued)

OTHER PUBLICATIONS

International Search Report and Written Opinion for PCT Application No. PCT/EP2013/076766, dated Jan. 15, 2014, 10 pages.

*Primary Examiner* — Ann Schillinger
(74) *Attorney, Agent, or Firm* — Westman, Champlin & Koehler, P.A.

(57) ABSTRACT

A valve prosthesis for replacing an atrioventricular valve of the heart is disclose, having a double ring body, on which heart cusps are fastened and that comprises a ventricle-side ring and an atrium-side ring, wherein the ventricle-side ring has an oval shape, and wherein anchors projecting substantially radially outward are arranged on the ventricle-side ring.

5 Claims, 2 Drawing Sheets

(58) Field of Classification Search
CPC .. A61F 2250/0039; A61F 2/07; A61F 2/2487; A61F 2/848; A61F 2002/8483
See application file for complete search history.

(56) References Cited

U.S. PATENT DOCUMENTS

| | | | |
|---|---|---|---|
| 2011/0137397 A1* | 6/2011 | Chau | A61F 2/2418 623/1.11 |
| 2012/0078353 A1* | 3/2012 | Quadri | A61F 2/2418 623/2.11 |
| 2012/0078360 A1 | 3/2012 | Rafiee | |

FOREIGN PATENT DOCUMENTS

| | | |
|---|---|---|
| EP | 1 994 913 A2 | 11/2008 |
| WO | 01/62189 A1 | 8/2001 |
| WO | 01/64137 A1 | 9/2001 |
| WO | 2004/019825 A1 | 3/2004 |
| WO | 2007/048529 A1 | 5/2007 |
| WO | 2007/051620 A1 | 5/2007 |
| WO | 2009/033469 A1 | 3/2009 |
| WO | 2012/095116 A | 7/2012 |
| WO | 2012/127309 A1 | 9/2012 |

\* cited by examiner

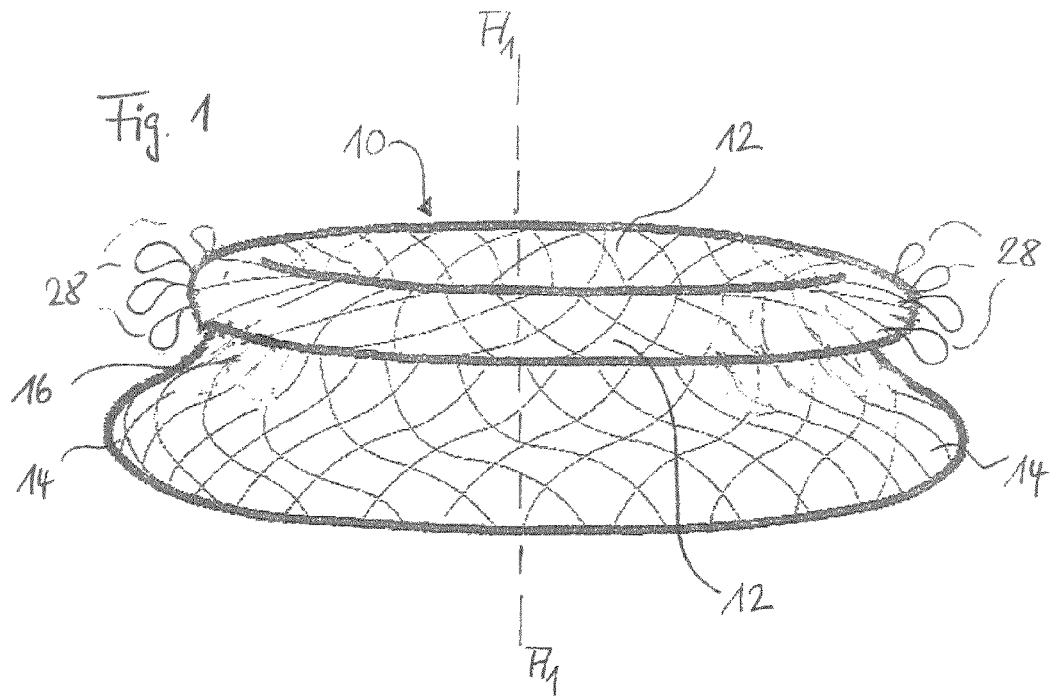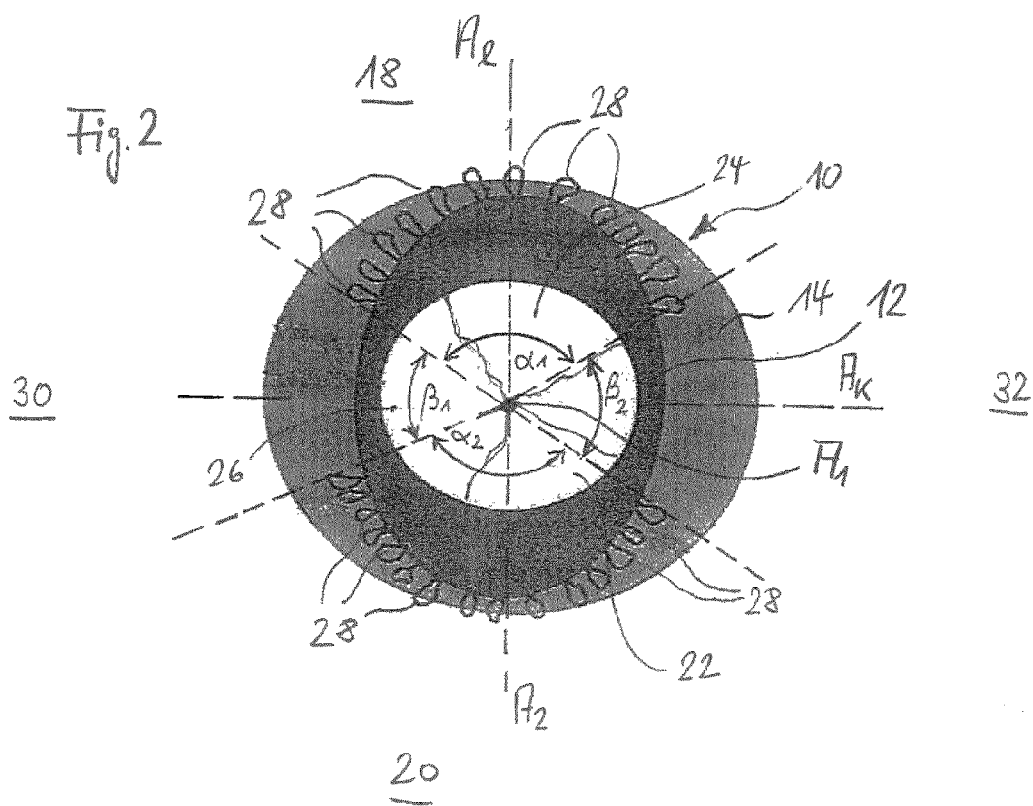

VALVE PROSTHESIS FOR THE REPLACEMENT OF AN ATRIOVENTICULAR VALVE

CROSS-REFERENCE TO RELATED APPLICATION

This Application is a Section 371 National Stage Application of International Application No. PCT/EP2013/076766, filed 16 Dec. 2013 and published as WO 2014/095761 A1 on 26 Jun. 2014, in English, the contents of which are hereby incorporated by reference in their entirety.

The invention relates to a valve prosthesis for the replacement of an atrioventricular valve of the heart, that is, the mitral valve or the tricuspid valve.

WO 2012/095116 A1 describes a valve prosthesis for replacing an atrioventricular valve of the heart with an annular body from which anchoring parts extend axially in such a manner that they can be brought into anchoring engagement with tissue such as, e.g., tendinous cords by rotating the annular body.

For patients with a functional defect of a heart valve an open surgical intervention on the heart for inserting a valve prosthesis (replacement valve) is frequently associated with elevated risks on account of the general state of the patient, so that heart valve prostheses are increasingly implanted with minimal invasion with a catheter.

The prior art knows the use of stents for this in which replacement heart cusps are fastened that can be greatly compressed for introduction via a catheter and in this manner can be advanced via the catheter to the site of the heart valve to be replaced and released there. The stent, that can be, for example, expanded by balloon or be self-expandable, develops a radial spreading force in the released state that brings about or at least furthers an anchoring of the replacement valve prosthesis. For such an anchoring of the valve prosthesis a replacement aorta valve is especially suited that can be anchored with radial spreading force at the site of the dysfunctional aorta valve. Cf. for the prior art in this regard, e.g., EP 1 994 913 A2; EP 1 469 797 B1; EP 1 259 195 B1; WO 2007/051620 A1; WO 2007/048529 A1; EP 1 980 220 A1; WO 01/64137 A1; EP 1 225 510 B3; and U.S. Pat. No. 5,411,552.

However, the mitral valve of the heart, that is, the valve between the left atrium and the left ventricle is poorly suited for a replacement prosthesis that is substantially non-positively (frictionally) anchored on site by the radial spreading force of a stent since a widening of the annulus is to be avoided.

WO 2012/127309 A1 describes a valve prosthesis with a double annular body in which the rings have different diameters and one ring should have an oval shape.

The invention has the basic task of making a valve prosthesis for the replacement of an atrioventricular valve available that can be implanted by a catheter and makes possible a stable and orthotropic positioning and anchoring.

A valve prosthesis in accordance with the invention for solving this task is described in claim 1. Advantageous embodiments of the valve prosthesis are described in the dependent claims.

A valve prosthesis for replacing an atrioventricular valve of the heart is provided with a double annular body on which heart cusps are fastened and which comprises an annulus on the ventricle side and an annulus on the atrium side, whereby the annulus on the ventricle side is provided on its outer circumference only in selected sectors with anchors standing substantially radially outward, while at least one sector of the annulus remains free of such anchors. That sector of the annulus remains free of anchors that is located in the area of the outflow passage given a proper use of the valve prosthesis in the heart. E.g., when the valve prosthesis is used between the left atrium and the left cardiac ventricle this outflow passage is the access to the aorta. These anchors, that serve to support the valve prosthesis in the area of the annulus between the atrium and the ventricle, are therefore arranged in such a manner that the blood flow from the ventricle into the outflow passage (e.g., the aorta or the pulmonary artery) remains as free as possible from wire hindrances. Such hindrances not only reduce the blood throughput but are also to be kept out of areas of heavy blood flow for biochemical reasons.

A preferred variant of the valve prosthesis provides that an annulus or bead is formed on the ventricle side and on the atrium side on a double annular body that is provided with heart cusps, whereby the annulus on the ventricle side is not perfectly circular relative to its central axis but rather has a reduced diameter in at least one sector. This sector with reduced diameter is positioned in such a manner during the insertion of the valve prosthesis in the heart that it is located in the area of the inflow to an outflow passage (e.g., aorta or pulmonary artery) in such a manner that the blood flow into the outflow passage of the ventricle is hindered as little as possible while the areas of the ventricle-side annulus with a larger diameter serve to support the valve prosthesis in other areas on the ventricle-side of the annulus.

The annulus can also be a ring disk in all exemplary embodiments.

The cited anchors and the cited support are rounded off on their ends coming in engagement with cardiac tissue in all exemplary embodiments of the valve prosthesis, for example, the anchors are loop-shaped. The anchors and the cited support are preferably directed substantially radially outward (in relation to the central axis of the prosthesis), whereby they can also be bent in the axial direction toward the annulus so that the anchors and the support have a hooked shape with an acute angle between the anchor and the central axis of the prosthesis.

In general, the valve prosthesis preferably has a shape approximately like a diabolo with an area of reduced diameter located axially approximately in the middle that is constructed in such a manner that it can be positioned when inserted between the atrium and the ventricle in the area of the annulus.

An embodiment of the valve prosthesis provides that the double annular body is adapted to not produce any radial spreading force that greatly widens the valve annulus when used in the valve annulus of the heart. A low spreading force that centers the double annular body in the valve annulus is nevertheless useful.

Other embodiments of the valve prosthesis provide that the double annular body is formed from a braiding, in particular from a material with shape memory.

The double annular body can be expanded by a balloon or be self-expandable.

If an "oval" shape is mentioned in conjunction with the valve prosthesis, this functionally means that the particular structural part, e.g., the cited ring, is shaped in such a manner that the structural part or the ring has at least one area with a reduced diameter that is to be arranged in such a manner when inserted in the area of the outflow passage of the cardiac chamber (e.g., aorta or pulmonary artery) that the blood flow is hindered as little as possible in this area by components of the valve prosthesis. Therefore, the ring cannot only be oval in the narrower sense of the word but also oval "on one side", that is, approximately kidney-shaped.

An exemplary embodiment of the invention is explained in detail in the following with reference made to the drawings. In the drawings:

FIG. 1 shows a perspective lateral view of a valve prosthesis,

FIG. 2 shows a top view onto the valve prosthesis in accordance with FIG. 1 in the direction of the central axis $A_1$ of the valve prosthesis.

Figure 3:
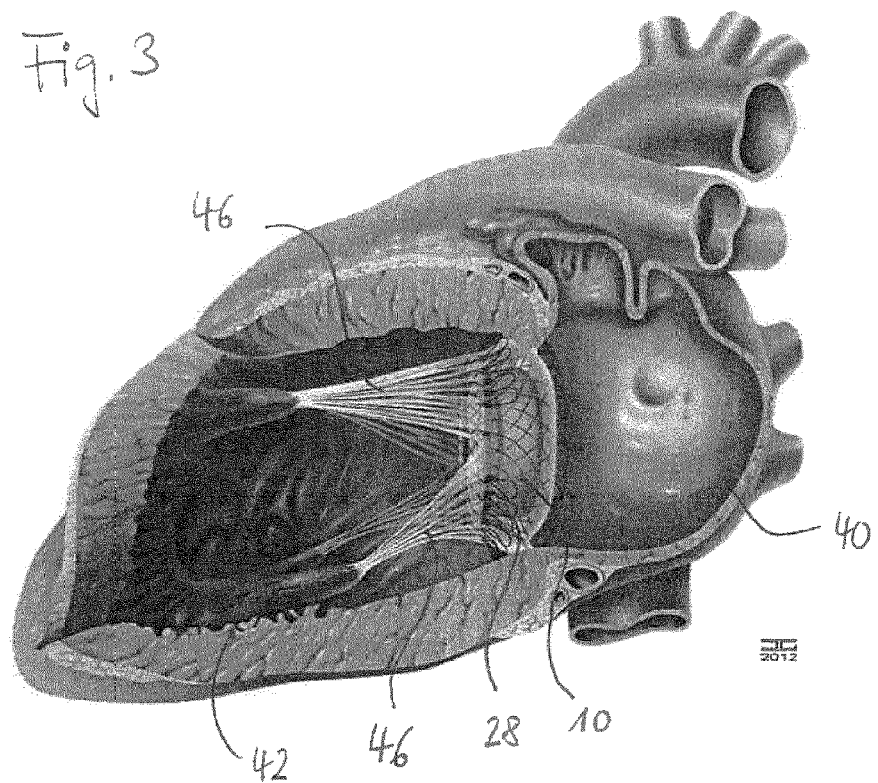
FIG. 3 shows a valve prosthesis in accordance with the FIGS. 1 and 2 in situ in the heart.

The valve prosthesis shown in the figures for replacing an atrioventricular heart valve comprises a double annular body 10 in which heart cusps are fastened. Known systems of the prior art can be used as such for the heart cusps, e.g., cusps of pericardium or, e.g., heart valves obtained from the heart of a pig, that are sewn in the double annular body. Such an arrangement of heart cusps in a stent-like structure are known as such.

The double annular body 10 is formed from a wire braiding and the elastic properties of the wire and the dimensions of the double annular body 10 are selected in such a manner that the double annular body does not produce any radial spreading force that substantially widens the natural valve annulus when used to replace, e.g., a mitral valve or a tricuspid valve—differently than is customary with a stent—but rather produces only a slight spreading force that brings about a centering of the double annular body 10 in the annulus.

A metal with shape memory such as nitinol can be used, e.g., for the wire braiding of the double annular body 10.

As FIG. 1 in particular shows, the double annular body 10 has two beads that are designated here as ventricle-side ring 12 and atrium-side ring 14. The designations "ventricle-side" and "atrium-side" refer to the positioning of the prosthesis in the heart.

The double annular body 10 has a middle area 16 between the ventricle-side ring 12 and the atrium-side ring 14, the diameter of which area is less than the diameter of these two rings. When used in the heart, this middle area 16 comes to rest in the annulus between the two heart chambers without substantially widening the annulus.

FIG. 2 shows a top view of the double annular body 10 in accordance with FIG. 1 from the direction of its middle axis $A_1$, from above in FIG. 1. In a corresponding manner FIG. 1 shows a view of the double annular body 10 in accordance with FIG. 2 from the side in FIG. 2, that is, e.g., from the right in the plane of the drawing.

According to the top view in FIG. 2 the atrium-side ring 14 is approximately circular whereas the ventricle-side ring 12 is approximately oval-shaped.

In FIG. 2 the area 18 can be designated with "above" and the area 20 with "below" relative to the inserted state in the heart.

In the top view according to FIG. 2 three heart cusps that are attached inside the double annular body 10 are provided with the reference numerals 22, 24, 26.

In accordance with the FIGS. 1 and 2 the ventricle-side ring 12 comprises anchors 28. These anchors 28 do not extend completely equidistantly over the entire circumference of the ventricle-side ring 12 but rather are limited to sectors of the ring. These sectors are designated in FIG. 2 with the angles $\alpha_1$ and $\alpha_2$. In a corresponding manner other sectors of the approximately oval-shaped, ventricle-side ring 14 are free of anchors and in the exemplary embodiment according to FIG. 2 these other sectors characterized with the angles $\beta_1$ and $\beta_2$.

When used in the heart the valve prosthesis is positioned in such a manner that a sector free of anchors 28 (that is, a sector according to one of the angles $\beta_1$ and $\beta_2$) is positioned in the area of an outflow passage (not shown) of the heart so that no anchor 28 is located in the area of the main blood flow that runs into the outflow passage of the chamber. When the valve prosthesis is used between the left chamber and the left atrium the outflow passage is the entrance to the aorta. This left ventricular outflow passage is located, e.g., in FIG. 2 on the side characterized there with the reference numeral 30. Therefore, the reference numeral 32 characterizes the position of the lateral wall.

As FIG. 2 shows, in this exemplary embodiment the ventricle-side ring 12 has a long axis $A_l$ and a short axis $A_k$. A sector of the ventricle-side ring 12 that extends in accordance with the angle $\beta_1$ on both sides of the short axis $A_k$ is free of anchors 28 in order to keep the blood flow in the area 30 of the left ventricular outflow passage as free as possible of wire hindrances or the like. In the exemplary embodiment according to FIG. 2 the opposite sector according to the angle $\beta_2$ is also free of anchors. This takes place in the exemplary embodiment shown in order to facilitate the positioning of the valve prosthesis in the heart since there are two positions in this embodiment in which the above-cited aim of keeping the outflow passage free of hindrances by rotating the prosthesis in its axis $A_l$ with two positions can be achieved.

The anchors 28 support, in cooperation with the ventricle-side and the atrium-side ring, the valve prosthesis in the annulus. The anchors 28, that are loop-shaped in the exemplary embodiment shown (deviating somewhat from the drawing), are bent in such a hook shape (down in FIG. 1) that they extend approximately to the ventricle-side area of the annulus and are supported there so that in the closed state of the valve prosthesis the ventricle-side pressure is absorbed.

Therefore, in this embodiment the loop-shaped anchors 28 do not stand exactly radially relative to the central axis $A_l$ of the double annular body 10 but rather form an acute angle with this central axis in the direction of the middle area 16 of the double annular body 10.

FIG. 3 shows a valve prosthesis according to the FIGS. 1 and 2 in the inserted state between atrium 40 and ventricle 42 of a heart. The double annular body 10 is positioned with its middle area 16 with reduced diameter precisely on the annulus 44 between the atrium 40 and the ventricle 42.

The anchors 28 extend through the tendinous cords 46 and are supported in this exemplary embodiment on the ventricle side on the annulus 44.

Figure 4:
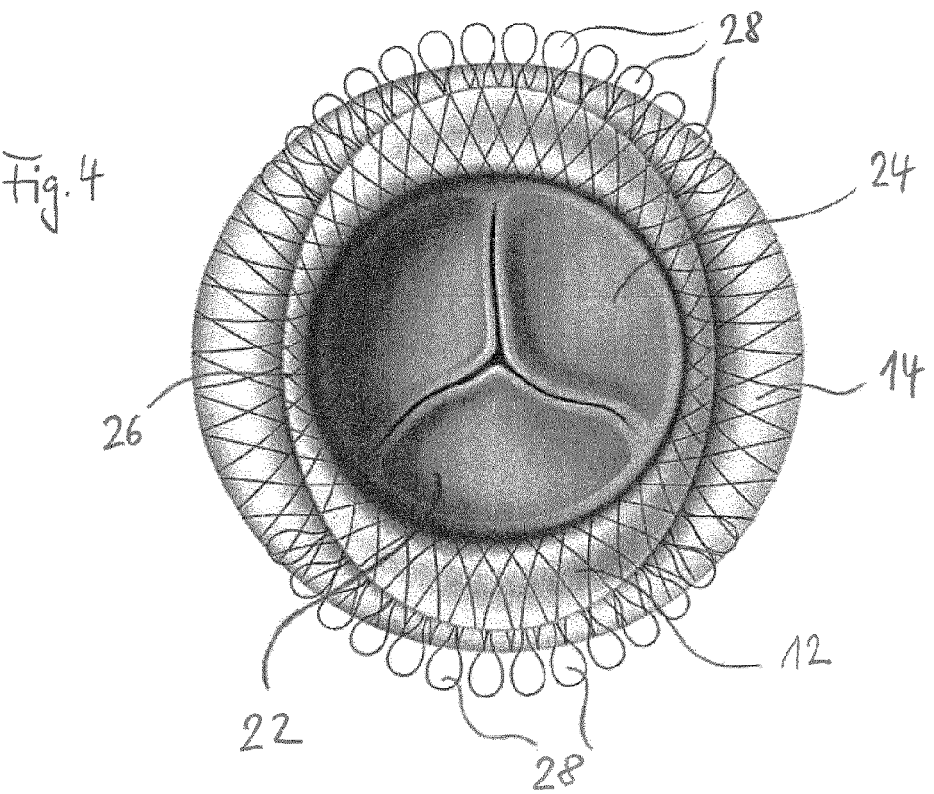
FIG. 4 shows an axial top view onto the valve prosthesis.

FIG. 4 shows the valve prosthesis in an axial top view with the heart cusps 22, 24, 26 in the closed state. In the figures the same parts are provided with the same reference numerals.

LIST OF REFERENCE NUMERALS 10 double annular body
12 ventricle-side ring
14 atrium-side ring
16 middle area (of 10)
18 "above"
20 "below"
22 heart cusp
24 heart cusp 26 heart cusp
28 anchors
30 left ventricular outflow passage
32 lateral wall
40 atrium
42 ventricle
44 annulus
46 tendinous cords
$A_1$ central axis (of 10)
$A_l$ long axis (of 12)
$A_k$ short axis (of 12)
$\alpha_1$ angle of a sector
$\alpha_2$ angle of a sector
$\beta_1$ angle of a sector
$\beta_2$ angle of a sector

The invention claimed is:

1. A valve prosthesis for replacing an atrioventricular valve of the heart, comprising:
  a double ring body, on which heart cusps are fastened;
  a ventricle-side oval ring which has an oval shape in such a manner that the ring has at least one area with a reduced diameter; and
  an atrium-side ring,
  wherein the ventricle-side oval ring has a long axis and a short axis being perpendicular to each other and intersecting on a central axis of the valve prosthesis, wherein the length of the long axis and the length of the short axis are defined by intersections with the diameter of the ventricle-side oval ring, wherein the length of the long axis is longer than the length of the short axis,
  wherein the ventricle-side oval ring is characterized in that anchors projecting radially outward are arranged on the ventricle-side oval ring,
  wherein the double ring body has a middle area between the ventricle-side oval ring and the atrium-side ring whose diameter is less than respective diameters of the ventricle-side oval ring and of the atrium-side ring,
  wherein the diameter of the ventricle-side oval ring is less than the diameter of the atrium-side ring, and
  wherein the diameter of the middle area is configured according to the annulus of the atrioventricular valve to be replaced, such that when the double ring body is used in the heart the middle area comes to rest in the annulus between a ventricle-side heart chamber and an atrium-side heart chamber without widening the annulus,
  wherein the anchors are provided only in sectors of the ring that are not located in the area of an outflow passage of a heart chamber;
  wherein the anchors are arranged only in sectors of the ventricle-side oval ring through whose angles the longer axis of the ring runs; and
  wherein the angles of the sectors are smaller than 160°.

2. The valve prosthesis according to claim 1, characterized in that the anchors are loop-shaped.

3. The valve prosthesis according to claim 1, characterized in that the double ring body is formed from a braiding and a material with shape memory.

4. The valve prosthesis according to claim 1, characterized in that the double ring body can be expanded by balloon.

5. The valve prosthesis according to claim 1, characterized in that the double ring body can be self-expanded.

* * * * *